United States Patent
Rock et al.

(10) Patent No.: US 6,898,462 B2
(45) Date of Patent: May 24, 2005

(54) DEFIBRILLATOR/MONITOR WITH PATIENT SPECIFIC TREATMENT ALGORITHMS

(75) Inventors: Joseph E. Rock, Littleton, MA (US);
Alfred Langguth, Hudson, NH (US);
Michael F Nakagawa, Cambridge, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 435 days.

(21) Appl. No.: 10/140,665

(22) Filed: May 8, 2002

(65) Prior Publication Data

US 2003/0212437 A1 Nov. 13, 2003

(51) Int. Cl.[7] .......................... A61N 1/362; A61N 1/39
(52) U.S. Cl. .................... 607/4; 607/5; 607/9; 607/14
(58) Field of Search ............................ 607/4, 5, 9, 14, 607/15, 30, 32

(56) References Cited

U.S. PATENT DOCUMENTS

| | | | |
|---|---|---|---|
| 5,156,148 A | 10/1992 | Cohen ......................... 128/419 |
| 5,405,362 A | 4/1995 | Kramer et al. ................ 607/5 |
| 5,456,691 A * | 10/1995 | Snell ........................... 607/30 |
| 5,517,405 A | 5/1996 | McAndrew et al. .......... 706/45 |
| 5,607,460 A * | 3/1997 | Kroll et al. ................... 607/30 |
| 5,716,382 A * | 2/1998 | Snell ............................ 607/30 |
| 6,356,785 B1 | 3/2002 | Snyder et al. ................. 607/5 |
| 6,493,579 B1 * | 12/2002 | Gilkerson et al. ............. 607/5 |
| 2003/0088284 A1 * | 5/2003 | Daynes et al. ................. 607/5 |

FOREIGN PATENT DOCUMENTS

| | | | |
|---|---|---|---|
| EP | 0 756 877 A | 2/1997 | .......... A61N/1/372 |
| WO | WO 94/00817 A | 1/1994 | .......... G06F/15/00 |
| WO | WO 02/26313 A | 4/2002 | ............ A61N/1/39 |

* cited by examiner

Primary Examiner—Carl Layno
(74) Attorney, Agent, or Firm—Tony Piotrowski

(57) ABSTRACT

An interactive apparatus which includes (a) a processing unit automatically implementing a cardiac treatment algorithm, by using detected signals from a patient and the cardiac treatment algorithm, to output a recommended treatment on an output device; and (b) an input device inputting a selection comprising an acceptance or a rejection of the recommended treatment, wherein if the selection comprises an acceptance, then the processing unit outputs instructions and further implements the treatment algorithm using the recommended treatment, wherein if the selection comprises a rejection, then the processing unit outputs an alternative recommended treatment on the output device, subject to acceptance or rejection by the input device.

46 Claims, 8 Drawing Sheets

DEFIBRILLATOR/MONITOR WITH PATIENT SPECIFIC TREATMENT ALGORITHMS

BACKGROUND OF THE INVENTION

During a resuscitation attempt, a rescuer using a defibrillator must quickly recognize dysrhythmias and recall complex treatment algorithms that are dependent on the particular anomaly present. Further, because medications are typically administered during a resuscitation attempt, specific patient information (such as age and weight) require that the rescuer integrate this information into the treatment of the patient.

Because of the complex nature of conducting a resuscitation, it is desirable to simplify the process as much as possible, leaving as little room for error on the part of the rescuer as possible.

One way the rescue process has been simplified is by "treatment algorithms." A treatment algorithm is a flowchart that the rescuer can follow which dictates step by step what course of action the rescuer should do in consideration of the condition of the patient. At certain points in the flowchart, a "branch point" is reached in which a decision is made about the patient's condition. For example, depending on the particular type of heart rhythm detected, different steps should be taken.

Prior art defibrillators have attempted to electronically implement the treatment algorithms by displaying instructions so the rescuer can follow these instructions step by step without having to rely on memory. One such prior art device is described in U.S. Pat. No. 5,405,362 to Kramer. However, one drawback of prior art systems such as Kramer is that the rescuer is limited at how much discretion he has during the implementation of the flowchart. For example, if such a system detects an asystolic condition, it will automatically proceed to implement the algorithm for Asystole, even though the rescuer desires to proceed as if the actual rhythm is bradycardic. If the rescuer desires not to accept the defibrillator's conclusions about where on the treatment flowchart to proceed, the rescuer will have to proceed manually without the aid of the system.

Therefore, what is needed is a system that allows a rescuer to administer a treatment algorithm automatically, but can override the system's recommendations at any time, and continue to receive assistance from the system.

SUMMARY OF THE INVENTION

In an exemplary embodiment, the present invention provides for an interactive defibrillator which automatically calculates and outputs recommended treatments based on a predefined treatment algorithm and detected signals from the patient, and allows a rescuer to choose whether to accept the recommended treatment or pursue an alternative treatment based on the algorithm.

In one embodiment, the present invention is achieved by providing an apparatus, including a processing unit continuously and automatically implementing a cardiac treatment algorithm, by using detected signals from a patient and the cardiac treatment algorithm, to output a recommended treatment on an output device; an input device for inputting a selection comprising an acceptance or a rejection of the recommended treatment, wherein if the selection comprises an acceptance, then the processing unit outputs instructions and further implements the treatment algorithm using the recommended treatment, wherein if the selection comprises a rejection, then the processing unit outputs an alternative recommended treatment on the output device, subject to acceptance or rejection by the input device.

The apparatus also includes a storage device storing all items outputted on the output device and inputted on the input device; a storage device storing all detected signals; a connector receiving a portable storage device storing the cardiac treatment algorithm; a printer printing a log of all items outputted on the output device and inputted on the input device, wherein the treatment algorithm comprises a flowchart, wherein the input unit inputs a patient's weight, age and other relevant physical findings, wherein the processing unit calculates a dosage of medication using the algorithm and the input weight, age and other relevant physical findings, wherein the outputted instructions comprise the calculated dosage of medication, wherein the output unit outputs a time left before another dosage of medication should be administered.

BRIEF DESCRIPTION OF THE DRAWINGS

The various objects and advantages of the invention will become apparent and more readily appreciated from the following description of the preferred embodiments, taken in conjunction with the accompanying drawings of which.

DESCRIPTION OF THE PREFERRED EMBODIMENTS

Figure 1:
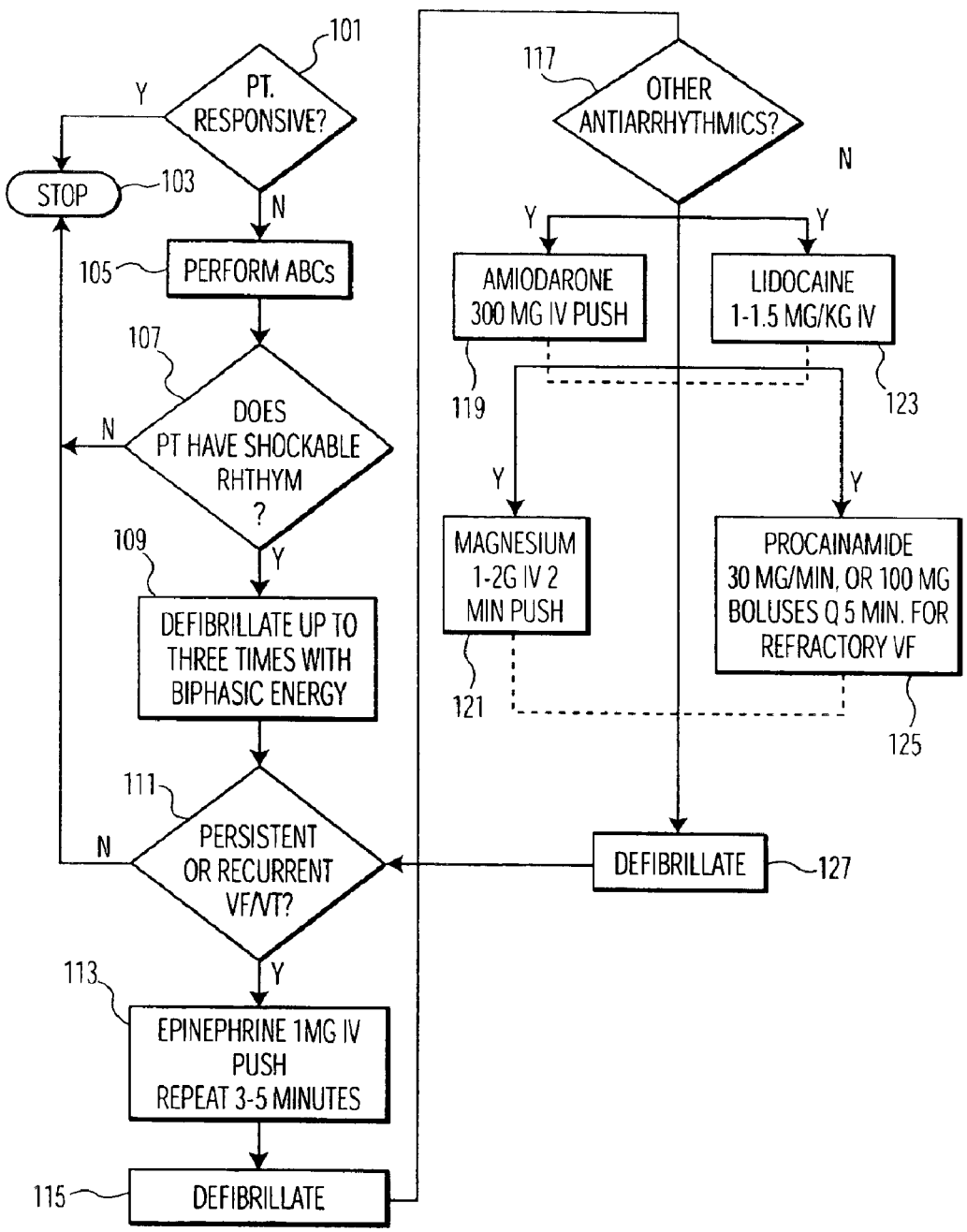
FIG. 1 is an example of a treatment algorithm flowchart.

Reference will now be made in detail to the present preferred embodiments of the present invention, examples of which are illustrated in the accompanying drawings, wherein like reference numerals refer to the like elements throughout.

The present invention provides for an interactive cardiac resuscitation system including a defibrillator. The defibrillator contains an output device, such as an LCD display, to display instructions to a rescuer. Input devices, for example buttons, a keyboard, a touch-screen display on the LCD, can be used so that the rescuer can communicate with the system. Further, detectors such as monitoring pads are connected between the patient and the system, so that the system can receive the patient's vital signs, such as an ECG or pulse signal.

The system electronically stores a treatment flowchart in electronic form. Based on the cardiac signals, the defibrillator consults the treatment flowchart and determines which paths to take, and then recommends treatments in the output device.

Thus the system automatically implements the treatment flowchart by navigating the flowchart based on the detected signals and outputting instructions contained in the flowchart at each node. The system can automatically adjust parameters based on the instructions, for example the shock energy administered can be automatically set by the system. Thus, instead of a rescuer having to memorize the flowchart, the system can automatically implement it, resulting in a more accurate treatment.

The rescuer may choose to accept the recommended treatment or override the recommendations, and choose an alternative point in the treatment algorithm to proceed. This choice can be made by using the input devices on the system.

FIG. 1 illustrates one example of a treatment algorithm flowchart. This particular algorithm starts at operation 101, which determines whether the patient is responsive. If the patient is responsive, then the treatment proceeds to operation 103 which stops further treatment. If the patient is determined not to be responsive in operation 101, then the treatment proceeds to operation 105 where the rescuer performs the ABC's. The "ABC's" are known to rescuers as "airway, breathing, and circulation." In other words, a rescuer would open the patient's airway using a head-tilt/chin-lift, look for chest rise and listen and feel for active breathing, and then check the patient's carotid pulse. From operation 105, the treatment then proceeds to operation 107 which determines whether the patient has a shockable rhythm. If operation 107 determines that the patient does not have a shockable rhythm, then the treatment proceeds to operation 103, which stops further treatment (or gives an option to select another algorithm). If operation 107 determines that the patient has a shockable rhythm, then the treatment proceeds to operation 109 where the rescuer applies electrical therapy to attempt defibrillation up to three times if necessary. From operation 109 the treatment proceeds to operation 111, which determines if there is persistent or recurrent VF/VT. If operation 111 determines that there is no persistent or recurrent VF/VT, then the treatment proceeds to operation 103, which stops further treatment (or gives an option to select another treatment).

If operation 111 determines that there is persistent or recurrent VF/VT (ventricular fibrillation/ventricular tachycardia), then the treatment proceeds to operation 113 wherein a push (i.e., inject at a reasonably fast rate) of epinephrine 1 mg IV is administered then repeated in 3–5 minutes. From operation 113, the treatment proceeds to operation 115 where the rescuer performs defibrillation.

From operation 115, the treatment proceeds to operation 117, which determines if the user would like to use other antiarrhythmics. If operation 117 determines that the user would like to use other antiarrhythmics, then the rescuer can choose to proceed to either: operation 119 where he would administer Amioderone 300 mg IV; operation 123 where he would administer lidocaine 1–1.5 mg/kg IV; operation 121 where he would administer magnesium 1–2 g IV 2 minute; or operation 125 where he would administer procainamide 30 mg/min or 100 mg boluses q 5 minute (every five minutes) for refractory VF. From operations 119, 121, 123, and 125, the treatment then proceeds to operation 127 where the rescuer performs defibrillation on the patient. From operation 127, the treatment proceeds to operation 111 where the process continues therein.

Please note that this is just one example of a treatment algorithm, and many others exist. Most notably, the American Heart Association (AHA) releases updated comprehensive algorithms periodically, known as the "AHA Guidelines for CPR/ECC." Also please note that the algorithm illustrated in FIG. 1 is merely an example and is not intended for actual use.

Figure 2:
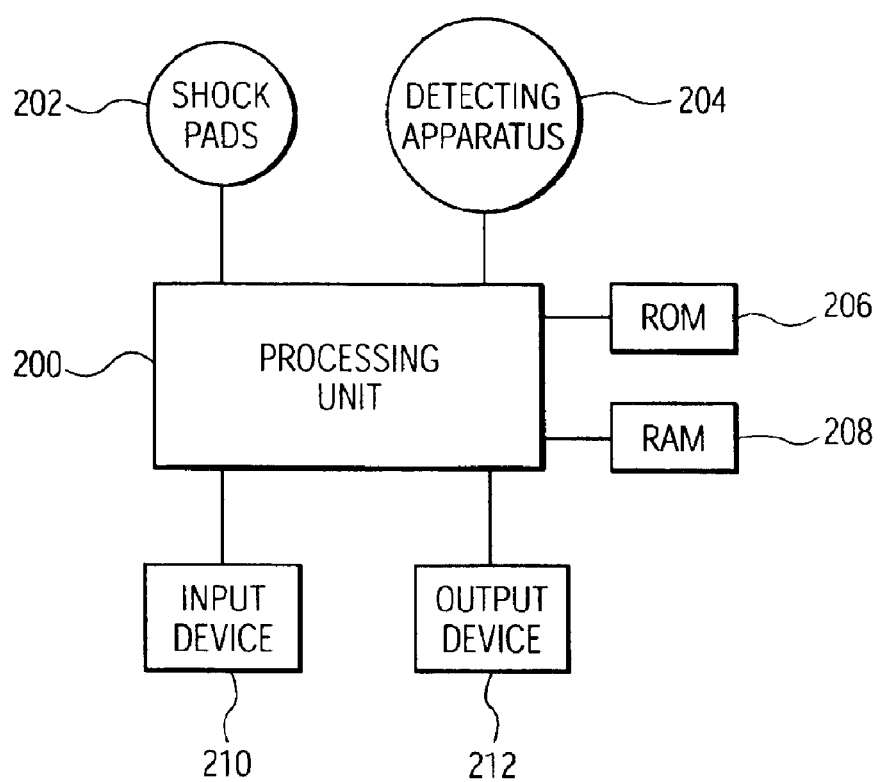
FIG. 2 is a diagram of one example of apparatus used to implement the present invention.

FIG. 2 is a diagram of one example of apparatus used to implement the present invention. Note that this is only one example of a general configuration, and any other applicable configuration can be used.

The shock apparatus 202 is connected to a processing unit 200 and is used to administer the actual electric therapy to the patient. The amount of energy applied to the therapy pads is controlled by the processing unit 200 and is based on a treatment in progress (to be discussed below). A detecting apparatus 204 is used to detect vital signs from the patient. For example, the detecting apparatus 204 can comprise a pad to detect the patient's pulse signals, or a monitoring pad to detect an ECG signal.

The processing unit 200 is the general unit, which handles all of the processing and inputs/outputs. The processing unit 200 also may include any other conventional apparatus needed to operate the system, for example an amplifier (not pictured) for use with the actual shock pads 202, and an analog to digital converter (not pictured) receiving the signals from a detecting apparatus 204. The processing unit receives the signals from the detecting apparatus 204 and analyzes the signals to identify particular characteristics, for example the type of cardiac rhythm detected.

A ROM 206 (or any other type of non-volatile memory can be used) stores system programs and data, such as the treatment algorithms. A RAM 208 is used for general purposes, for example to store the present operating conditions of the system, and a pointer pointing to the present location in the chart.

An output device 212 is connected to the processing unit 200 and can typically comprise an LCD display. Other output devices, such as CRT display, LEDs, audio, or any other output device can be used as well. An input device 210 is connected to the processing unit 200 and is used to input parameters and information from the rescuer. The input device can typically comprise buttons or a keyboard, but any other conventional input device can be used as well, including using a display that is touch sensitive. Further, note that it is possible that in one embodiment of the present invention, the output device 212 and input device 210 can be housed within the same physical unit.

Figure 3:
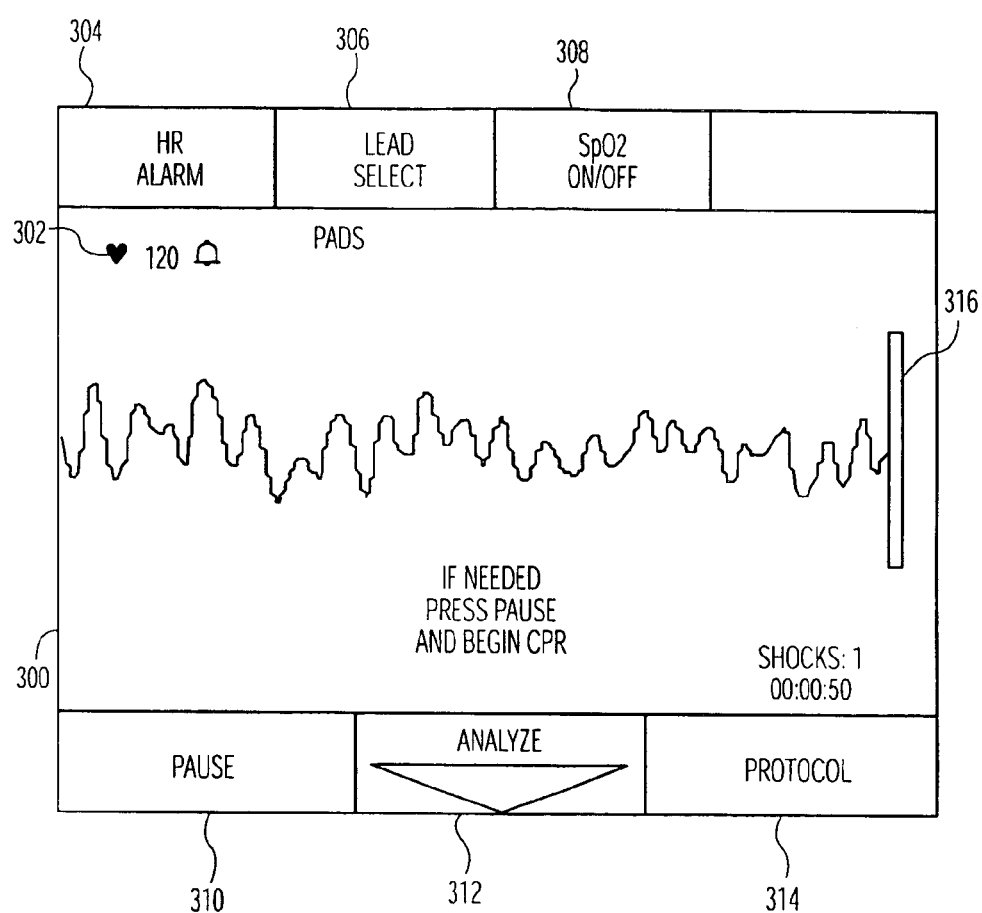
FIG. 3 is a sample display illustrating a sample first output screen on the display.

FIG. 3 is a sample display illustrating a sample first output screen on the display. The display outputs a window 300 comprising all of the vital information regarding the patient's vital signs and the rescue attempt. The patient's pulse rate 302 is displayed (120 beats per minute). An HR alarm button 304 sets heart rate alarm thresholds, so that if the heart rate becomes faster than the high rate limit or slower than the low rate limit, then an alarm will sound. A lead select button 306 selects which ECG lead is used for background monitoring. An SpO2 button 308 selects whether or not the measurement of arterial oxygen saturation will be performed. A pause button 310 allows the rescuer to pause operation of the system. A protocol button 314 allows the rescuer to have the system immediately analyze the patient's signals and determine the type of rhythm detected and a recommended treatment. An analyze button 312 starts the device to immediately begin analyzing the heart rhythm for a shockable rhythm. An ECG graph 316 is displayed indicating the patient's ECG signals. Note that the configuration of buttons in FIG. 3 is merely one example of how relevant buttons can be selected and arranged on a display, and it can be appreciated that the layout can be achieved by a variety of other combinations.

Figure 4:
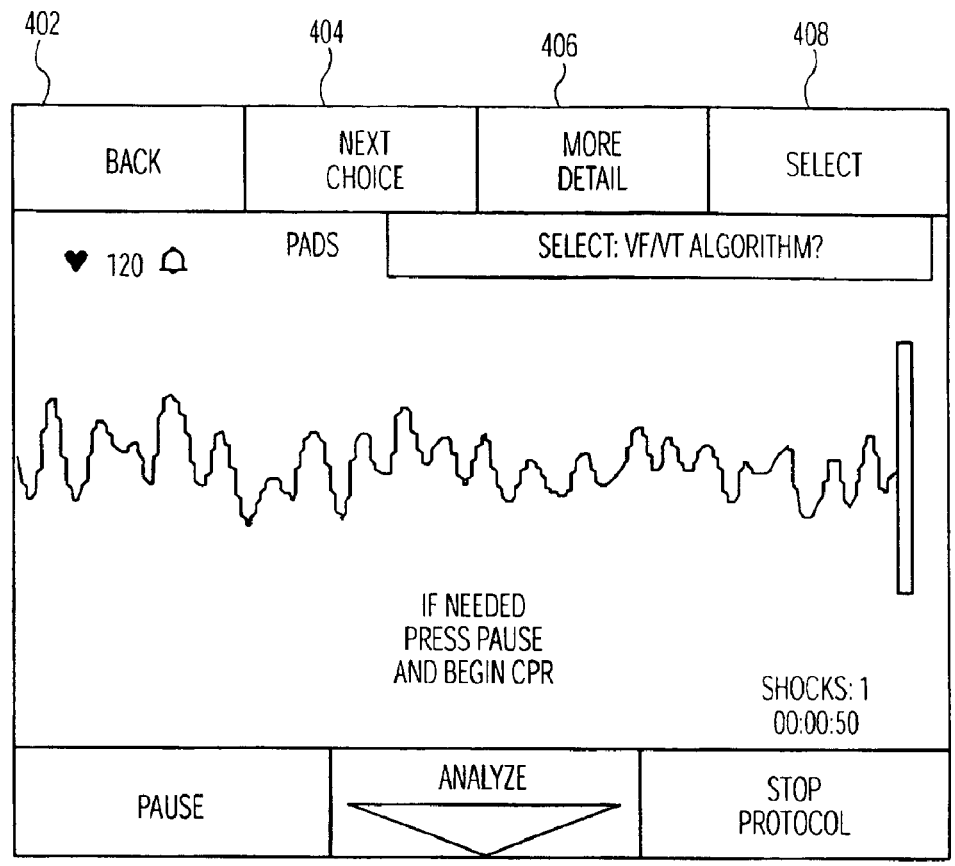
FIG. 4 is a sample display illustrating a sample second output screen on the display.

FIG. 4 is a sample display illustrating a sample second output screen on the display, after the protocol button 314 is pressed. An algorithm window 318 is displayed, which identifies the type of dysrhythmia detected. In this case, the algorithm window displays, "Select: VF/VT Algorithm." In this particular example, the system detected that the patient is undergoing a ventricular fibrillation or ventricular tachycardia. At this point, the rescuer can proceed with the treatment algorithm for the VF/VT dysrhythmia, or the rescuer can proceed as if the patient is undergoing another dysrhythmia.

Figure 5A:
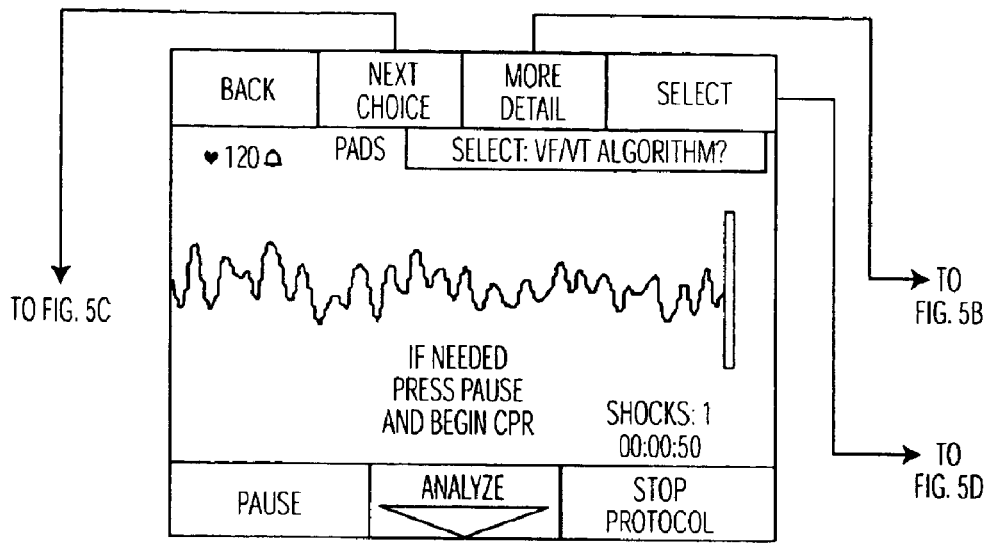
FIGS. 5A, 5B, 5C, and 5D are sample displays illustrating further output screens on the display.
Figure 5B:
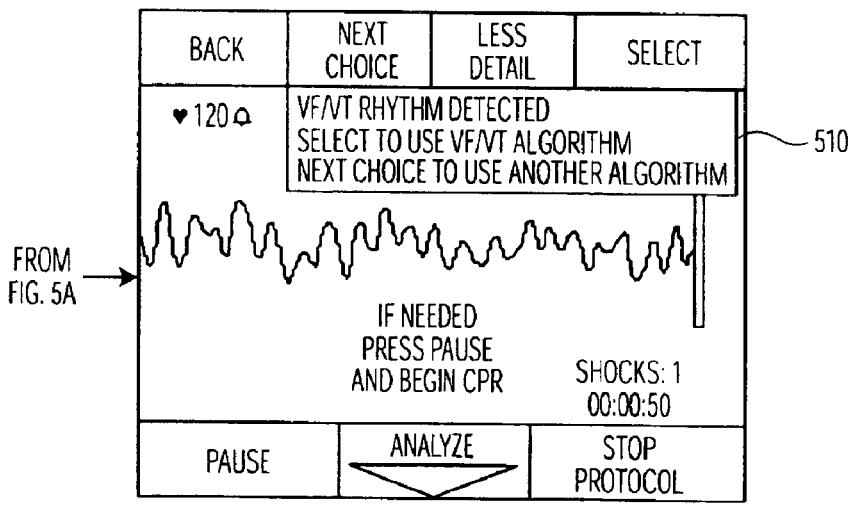

FIGS. 5A, 5B, 5C, and 5D are sample displays illustrating further output screens on the display. FIG. 5A is the same as FIG. 4. If the more detail button 406 is pressed, then the display in FIG. 5B is displayed. A detail window 510 indicates the type of rhythm detected, and instructions on how to proceed.

Figure 5C:
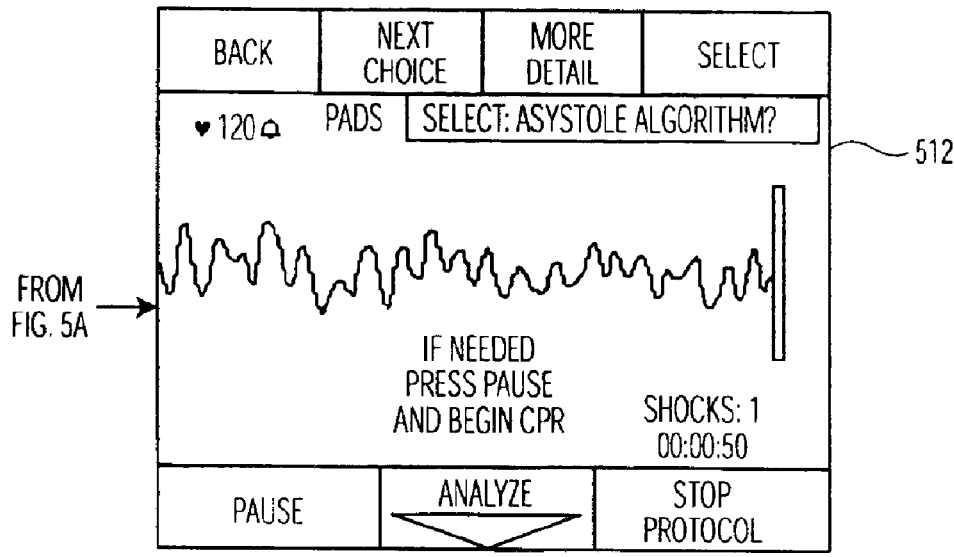
Figure 5D:
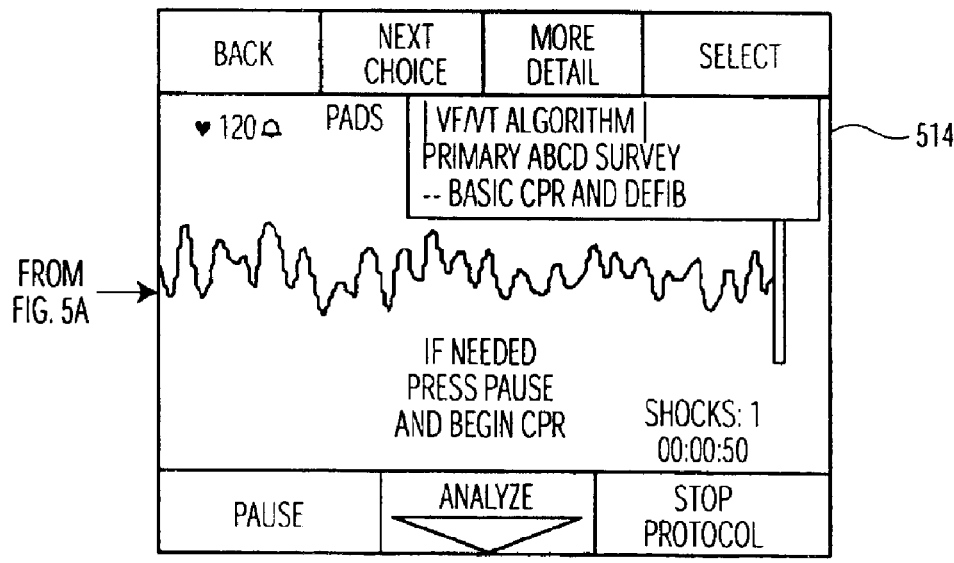

Referring back to FIG. 5A, if the next choice button is pressed, then the display shown in FIG. 5C is displayed. A choice window 512 is displayed which displays an alternative algorithm (also known herein as recommended treatment). If the next choice button is pressed again, another alternative algorithm (not pictured) is displayed. Referring back to FIG. 5A, if the select button is pressed, then the display shown in FIG. 5D is displayed. A selection window 514 is displayed which displays instructions to the rescuer on how to treat the patient based on the algorithm selected.

Using the display screens illustrated above, the rescuer is free to accept an automatic selection of algorithm to use, or in the alternative the rescuer may choose to select an alternative algorithm.

Figure 6:
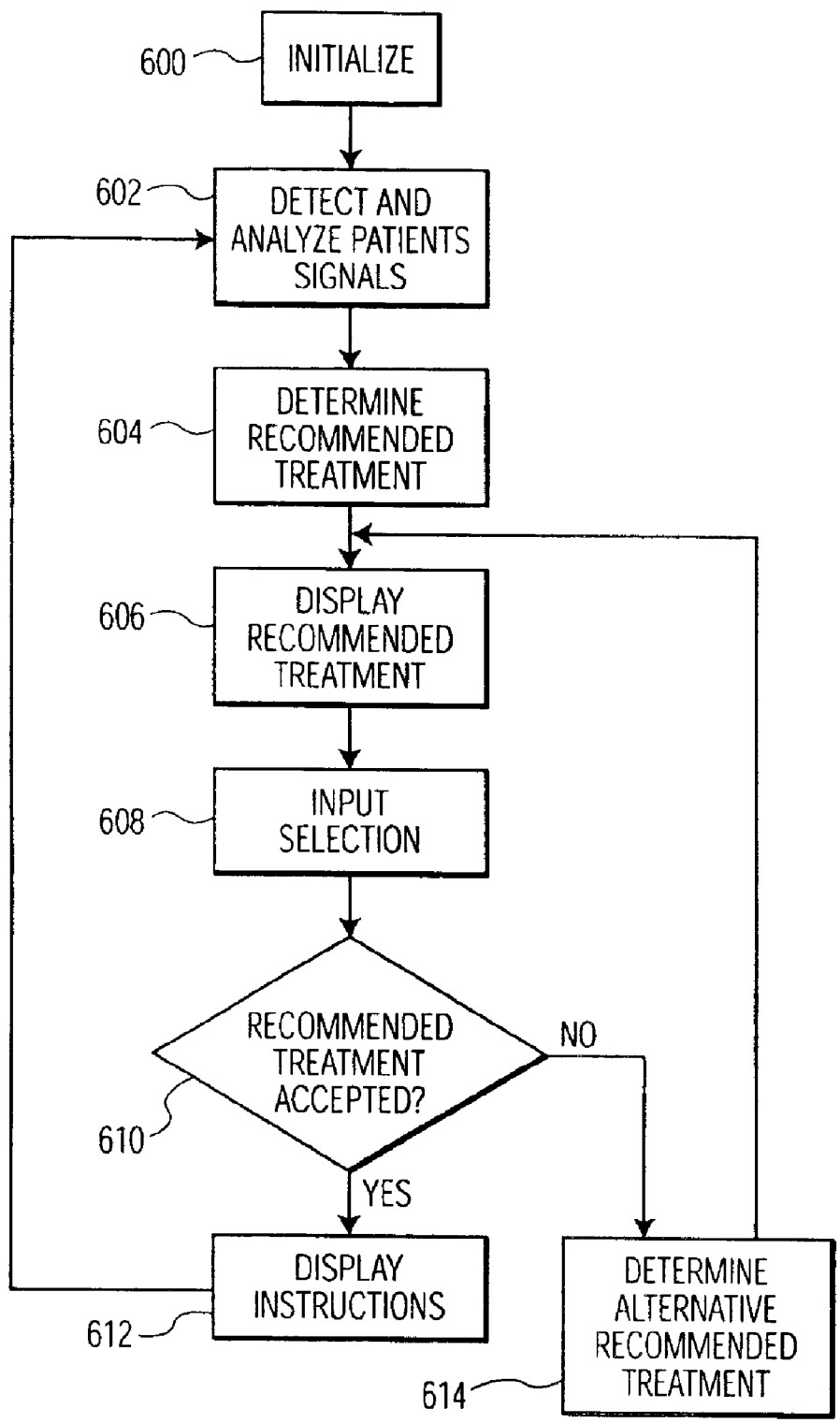
FIG. 6 is a flowchart illustrating the process of allowing a rescuer to select an alternative treatment.

FIG. 6 is a flowchart illustrating the process of allowing a rescuer to select an alternative treatment. Beginning with operation 600, the system initializes. The initialization may consist of pointing a pointer to a top of a treatment algorithm, and any other routine system functions a computer system needs to perform before executing a program.

After initialization, the process proceeds to operation 602 wherein the patient's vital signs are detected and analyzed. For example, the patient's ECG signals are received, and the type of dysrhythmia is determined. From operation 602, the process proceeds to operation 604 wherein using a determined dysrhythmia (or any other analysis of the patient's conditions) from operation 602, a recommended treatment is determined using the treatment algorithm. For example, the system may choose a branch on the treatment algorithm depending on the determined condition.

From operation 604, the process proceeds to operation 606, wherein the recommended treatment is displayed. The recommended treatment can comprise medications to be administered, shocks to be administered (including energy setting), physical resuscitation techniques, and any other treatment that can be administered to the patient. From operation 606, the process proceeds to operation 608, wherein a selection is inputted from the rescuer. The selection can comprises whether or not the rescuer accepts the recommended treatment.

In operation 610, a check is performed to see whether or not the rescuer accepts the recommended treatment. If the rescuer accepts the recommended treatment, then the process proceeds to operation 612, wherein the system displays instructions to the rescuer regarding implementing the recommended treatment. Also, the system updates a record of the patient's treatment history. For example, this can include updating the pointer pointing to the current location in the treatment flowchart to a new location. From operation 612, the process returns to operation 602 wherein the treatment continues.

If the check in operation 610 determines that the rescuer does not accept the recommended treatment, then the process proceeds to operation 614 wherein the system chooses an alternative recommended treatment based on an alternative location in the treatment flowchart. The alternative location can be determined by locating other locations in the flowchart that can be branched to based on the patient's conditions. From operation 614, the process returns to operation 610 wherein the (alternative) recommended treatment is displayed. Note that the rescuer can scroll through several alternative treatments using operations 608, 610, and 614, until the rescuer finds an acceptable treatment.

As an example of how the rescuer can override what the system recommends using the method illustrated in FIG. 6, please refer to FIG. 1. When the system reaches operation 111, it automatically detects whether there is persistent or recurrent VF/VT (operation 604). Let us assume there is no persistent of recurrent VF/VT. The system then determines the recommended treatment (operation 606) based on this detection, which would be to stop treatment based on the flowchart. This recommended treatment is outputted (operation 606). The rescuer then inputs this selection, accepting or rejecting the recommended treatment (operation 608). If the rescuer accepts this recommended treatment (determined in operation 610), then the system displays instructions on performing this recommended treatment (operation 612). In this case, the instructions displayed would be to stop further treatment or choose another algorithm.

On the other hand, if the rescuer does not accept the recommended treatment (determined in operation 610), then the system determines an alternative recommended treatment (operation 614). In this particular example, the alternative recommended treatment from FIG. 1 could be to proceed to operation 113, wherein epinephrine 1 mg is administered. The alternative recommended treatment would be displayed (operation 616) and the process continues therein. In this way, the rescuer is able to use the automated system, but can optionally override any recommendations at any point along the treatment process.

Another point in the treatment chart of FIG. 1 where the rescuer may choose to administer alternative treatments to those recommended is at operation 117. While the system may recommend one particular treatment (for example operation 119), the rescuer may choose to administer alternative treatments 123, 121, or 125.

Note that any time a treatment is recommended the rescuer has the ability to accept the recommended treatment, or proceed to an alternative recommended treatment. While the typical alternative recommended treatment comprises following alternative branches at a particular node, the rescuer also has the ability to proceed from any node on the treatment chart to any other node.

Moreover, while the system may automatically set parameters such as a shock energy to be administered to the patient, the rescuer can manually substitute his own values for any of these automatically set ones.

Further, in another embodiment, a treatment storage unit stores on a computer readable storage medium all that is displayed on the display unit (or just selected items that are displayed on the display unit) and/or inputted from the rescuer. The computer readable storage medium can comprise, for example, a floppy disk, CD-R, or any recordable storage medium. In this way, the treatment for each patient can be referred to later on, and can also be uploaded to another computer via the Internet or using a cable.

In another embodiment of the present invention, a printer attached to the defibrillator will print out everything that is displayed on the output device (or just selected items displayed on the output device). In this way, a hard copy is kept of what the rescuer has seen on the display for future reference.

In yet another embodiment of the present invention, the treatment algorithm can easily be updated by inserting a storage device into the defibrillator containing a treatment algorithm or algorithms. For example, a treatment algorithm can be stored on a floppy disk or on a flash memory card, thus the rescuer can easily insert the storage device into the defibrillator. The system can automatically read the algorithm stored on the storage device and implement it. This embodiment can be very useful in that new and revised treatment algorithms are released periodically. The algorithm can be stored in digital form, using a data structure comprising nodes of recommended treatments, and links to other nodes in the data structure combined with respective conditions for those links.

Figure 7:
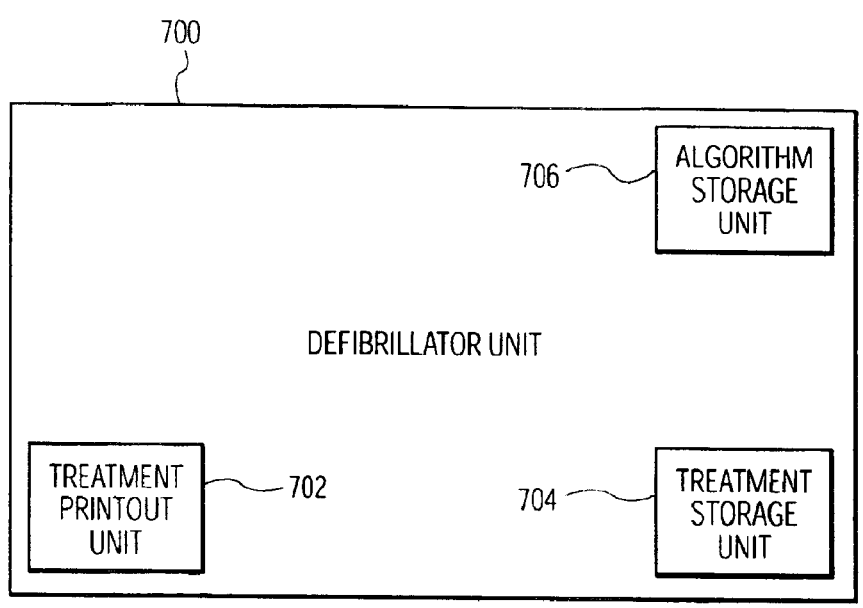
FIG. 7 is a diagram of one example of an apparatus used to implement the present invention with optional operations.

FIG. 7 is a diagram of one example of an apparatus used to implement the present invention with optional operations. The defibrillator unit 700 can comprise an optional treatment printout unit 702 (as discussed above), a treatment storage unit 704 (as discussed above), and an algorithm storage unit 706 (as discussed above), and any combination of these components.

In another embodiment of the present invention, the rescuer can input a patient's weight or estimated weight, and/or age or approximate age. The system can calculate medication and/or electrical therapy dosages based on the patient information. When the output device outputs instructions regarding administering medication, dosages will reflect the patient information. This presents the rescuer with the correct dosage while freeing the rescuer from having to perform these calculations, which are prone to estimation errors and thus inaccurate therapy doses. In addition, the output device can periodically output time intervals whereupon the rescuer needs to administer medication. For example, the output device can "count down" the time required for the next dosage of medication. In one embodiment, an audio signal (such as a human voice) may prompt the rescuer when it is time to administer the next dosage of medication.

Although a few preferred embodiments of the present invention have been shown and described it would be appreciated by those skilled in the art that changes may be made in these embodiments without departing from the principles and spirit of the invention, the scope of which is defined in the claims and their equivalents.

What is claimed is:

1. An apparatus, comprising:
   a processing unit automatically implementing a cardiac treatment algorithm, by using detected signals from a patient and the cardiac treatment algorithm, to output a recommended treatment on an output device; and
   an input device inputting a selection comprising an acceptance or a rejection of the recommended treatment,
   wherein if the selection comprises an acceptance, then the processing unit outputs instructions and further implements the treatment algorithm using the recommended treatment,
   wherein if the selection comprises a rejection, then the processing unit outputs an alternative recommended treatment on the output device, subject to acceptance or rejection via the input device.

2. An apparatus as recited in claim 1, further comprising a storage device storing items outputted on the output device and inputted via the input device.

3. An apparatus as recited in claim 1, further comprising a storage device storing detected signals.

4. An apparatus as recited in claim 1, further comprising a connector interfacing with a portable storage device storing the cardiac treatment algorithm.

5. An apparatus as recited in claim 1, further comprising a printing device printing a log of important items outputted on the output device and inputted on the input device.

6. An apparatus as recited in claim 1, wherein the treatment algorithm comprises a flowchart.

7. An apparatus as recited in claim 1, wherein the input unit inputs a patient's weight and age.

8. An apparatus as recited in claim 7, wherein the processing unit calculates a dosage of medication using the algorithm and the input weight and age.

9. An apparatus as recited in claim 7, wherein the processing unit calculates an electrical therapy using the algorithm and the input weight and age.

10. An apparatus as recited in claim 8, wherein the outputted instructions comprise the calculated dosage of medication.

11. An apparatus as recited in claim 9, wherein the outputted instructions comprise the calculated electrical therapy.

12. An apparatus as recited in claim 1, wherein the output unit outputs a time left before another dosage of medication should be administered.

13. An apparatus, comprising:
   a processing unit automatically implementing a cardiac treatment algorithm, by using detected signals from a patient and the cardiac treatment algorithm, to output a recommended treatment on an output device;
   an input device inputting a selection comprising an acceptance or a rejection of the recommended treatment,
   wherein if the selection comprises an acceptance, then the processing unit outputs instructions and further implements the treatment algorithm using the recommended treatment,
   wherein if the selection comprises a rejection, then the processing unit outputs an alternative recommended treatment on the output device, subject to acceptance or rejection by the input device;
   a storage device storing items outputted on the output device and inputted on the input device;
   a storage device storing detected signals;
   a connector interfacing with a portable storage device storing the cardiac treatment algorithm; and
   a printer printing a log of all items outputted on the output device and inputted on the input device,
   wherein the treatment algorithm comprises a flowchart,
   wherein the input unit inputs a patient's weight and age,
   wherein the processing unit calculates a dosage of medication using the algorithm and the input weight and age,
   wherein the outputted instructions comprise the calculated dosage of medication,
   wherein the processing unit calculates an electrical therapy using the algorithm and the input weight and age,
   wherein the outputted instructions comprise the electrical therapy using the algorithm and the input weight and age,
   wherein the output unit outputs a time left before another dosage of medication should be administered.

14. An apparatus, comprising:
  a processing unit automatically calculating a recommended treatment and an alternative treatment based on detected cardiac signals and a treatment algorithm;
  an output device outputting the recommended treatment and the alternative treatment; and
  an input device inputting a selection of the recommended treatment or the alternative treatment,
  wherein the processing unit calculates further treatments based on the selection and the algorithm.

15. An apparatus as recited in claim 14, wherein the treatment algorithm comprises a treatment flowchart.

16. A apparatus comprising:
  a processing unit automatically guiding a user through a cardiac treatment algorithm by monitoring signals detected from a patient and selections input from a user, and outputting recommended treatments on an output device; and
  an input device inputting a selection comprising an acceptance or a rejection of the recommended treatment,
  wherein if the selection comprises an acceptance, then the processing unit outputs instructions and further guides the user through the treatment algorithm using the recommended treatment,
  wherein if the selection comprises a rejection, then the processing unit outputs an alternative recommended treatment on the output device, subject to acceptance or rejection via the input device.

17. A method, comprising:
  automatically implementing a cardiac treatment algorithm, by using detected signals from a patient and the cardiac treatment algorithm, to output a recommended treatment; and
  inputting a selection comprising an acceptance or a rejection of the recommended treatment,
  wherein if the selection comprises an acceptance, then further outputting instructions and further implementing the treatment algorithm using the recommended treatment,
  wherein if the selection comprises a rejection, then further outputting an alternative recommended treatment, subject to acceptance or rejection by the rescuer.

18. A method as recited in claim 17, further comprising storing outputs and inputs.

19. A method as recited in claim 17, further comprising storing detected signals.

20. A method as recited in claim 17, further comprising interfacing with a portable storage device storing the cardiac treatment algorithm.

21. A method as recited in claim 17, further comprising printing a log of items outputted on the output device and inputted on the input device.

22. A method as recited in claim 17, wherein the treatment algorithm comprises a flowchart.

23. A method as recited in claim 17, further comprising inputting a patient's weight and age.

24. A method as recited in claim 23, further comprising calculating a dosage of medication using the algorithm and the input weight and age.

25. A method as recited in claim 23, further comprising calculating an electrical therapy using the algorithm and the input weight and age.

26. A method as recited in claim 24, wherein the outputted instructions comprise the calculated dosage of medication.

27. A method as recited in claim 25, wherein the outputted instructions comprise the calculated electrical therapy.

28. A method as recited in claim 17, further comprising outputting a time left before another dosage of medication should be administered.

29. A method, comprising:
  automatically calculating a recommended treatment and an alternative treatment based on detected cardiac signals and a treatment algorithm;
  outputting the recommended treatment and the alternative treatment; and
  inputting a selection of the recommended treatment or the alternative treatment,
  calculating further treatments based on the selection and the algorithm.

30. A method as recited in claim 29, wherein the treatment algorithm comprises a treatment flowchart.

31. A method, comprising:
  automatically guiding a user through a cardiac treatment algorithm by monitoring signals detected from a patient and selections input from a user, and outputting recommended treatments on an output device; and
  inputting a selection comprising an acceptance or a rejection of the recommended treatment,
  wherein if the selection comprises an acceptance, then outputting instructions and further guiding the user through the treatment algorithm using the recommended treatment,
  wherein if the selection comprises a rejection, then outputting an alternative recommended treatment on the output device, subject to acceptance or rejection by the user.

32. A computer readable storage, controlling a computer by:
  automatically implementing a cardiac treatment algorithm, by using detected signals from a patient and the cardiac treatment algorithm, to output a recommended treatment; and
  inputting a selection comprising an acceptance or a rejection of the recommended treatment,
  wherein if the selection comprises an acceptance, then further outputting instructions and further implementing the treatment algorithm using the recommended treatment,
  wherein if the selection comprises a rejection, then further outputting an alternative recommended treatment, subject to acceptance or rejection by the rescuer.

33. A computer readable storage as recited in claim 32, further comprising storing outputs and inputs.

34. A computer readable storage as recited in claim 32, further comprising storing detected signals.

35. A computer readable storage as recited in claim 32, further comprising interfacing with a portable storage device storing the cardiac treatment algorithm.

36. A computer readable storage as recited in claim 32, further comprising printing a log of items outputted on the output device and inputted on the input device.

37. A computer readable storage as recited in claim 32, wherein the treatment algorithm comprises a flowchart.

38. A computer readable storage as recited in claim 32, further comprising inputting a patient's weight and age.

39. A computer readable storage as recited in claim 38, further comprising calculating a dosage of medication using the algorithm and the input weight and age.

40. A computer readable storage as recited in claim 38, further comprising calculating an electrical therapy using the algorithm and the input weight and age.

41. A computer readable storage as recited in claim 39, wherein the outputted instructions comprise the calculated dosage of medication.

42. A computer readable storage as recited in claim 40, wherein the outputted instructions comprise the calculated electrical therapy.

43. A computer readable storage as recited in claim 32, further comprising outputting a time left before another dosage of medication should be administered.

44. A computer readable storage, controlling a computer by:
   automatically calculating a recommended treatment and an alternative treatment based on detected cardiac signals and a treatment algorithm;
   outputting the recommended treatment and the alternative treatment; and
   inputting a selection of the recommended treatment or the alternative treatment,
   calculating further treatments based on the selection and the algorithm.

45. A computer readable storage as recited in claim 44, wherein the treatment algorithm comprises a treatment flowchart.

46. A computer readable storage, controlling a computer by:
   automatically guiding a user through a cardiac treatment algorithm by monitoring signals detected from a patient and selections input from a user, and outputting recommended treatments on an output device; and
   inputting a selection comprising an acceptance or a rejection of the recommended treatment,
   wherein if the selection comprises an acceptance, then outputting instructions and further guiding the user through the treatment algorithm using the recommended treatment,
   wherein if the selection comprises a rejection, then outputting an alternative recommended treatment on the output device, subject to acceptance or rejection by the user.

* * * * *